United States Patent [19]

Fancher

[11] 4,097,605
[45] Jun. 27, 1978

[54] ALKYL THIOUREA MITICIDES

[75] Inventor: Llewellyn W. Fancher, Orinda, Calif.

[73] Assignee: Stauffer Chemical Company, Westport, Conn.

[21] Appl. No.: 742,157

[22] Filed: Nov. 15, 1976

Related U.S. Application Data

[63] Continuation of Ser. No. 597,104, Jul. 18, 1975, abandoned.

[51] Int. Cl.$^2$ .......................... A01N 9/12; A01N 9/20; C07C 157/09
[52] U.S. Cl. .................................. 424/322; 260/552 R
[58] Field of Search ...................... 260/552 R; 424/322

[56] References Cited

U.S. PATENT DOCUMENTS 3,584,993   6/1971   Myles et al. ........................ 8/165

OTHER PUBLICATIONS

Erickson, "J. Org. Chem.", vol. 21 (1956), pp. 483–484.
Schmidt et al., Chem. Abstracts, vol. 36 (1942), p. 4804(8).

Primary Examiner—V. D. Turner
Attorney, Agent, or Firm—M. Henry Heines; Michael J. Bradley

[57] ABSTRACT

Miticidally active compounds, which are defined by the following generic formula

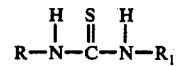

wherein R and R$_1$ in general are selected from the group consisting of benzhydryl, 3'-(2'-ethylhexoxy)-propyl, allyl, cyclohexyl, cycloheptyl, and alkyl, are described herein.

37 Claims, No Drawings

ALKYL THIOUREA MITICIDES

This is a continuation of application Ser. No. 597,104, filed July 18, 1975 now abandoned.

BACKGROUND OF THE INVENTION

Included among the many insecticidal and miticidal compounds available are various substituted thioureas. Such compounds and their biological properties are discussed in Hoskins, W. M., et al., *J. Econ. Ent.*, 33:6, 875–881 (1940), and Schroeder, D. C., *Chem. Reviews,* 55, 181–228 (1955).

BRIEF DESCRIPTION OF THE INVENTION

This invention relates to a class of substituted thioureas and to their use as miticides when used in a miticidally effective amount. More specifically, this invention relates to alkyl thioureas having the formula

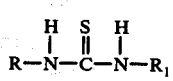

wherein —R is selected from the group consisting of benzhydryl, 3'-(2'-ethylhexoxy)-propyl, allyl, cyclohexyl, cycloheptyl, 1',3'-dimethylbutyl, and alkyl containing from 7 to 13 carbon atoms, inclusive; and where R is benzhydryl, $R_1$ is alkyl containing from 7 to 11 carbon atoms, inclusive; where R is 3'-(2'-ethylhexoxy)-propyl, $R_1$ is alkyl containing from 1 to 12 carbon atoms, inclusive; where R is allyl, $R_1$ is alkyl containing from 9 to 13 carbon atoms, inclusive; where R is cyclohexyl, $R_1$ is dodecyl; where R is cycloheptyl, $R_1$ is heptyl; where R is 1',3'-dimethylbutyl, $R_1$ is n-heptyl or dodecyl; where R is heptyl, $R_1$ is alkyl containing from 6 to 8 carbon atoms, inclusive; where R is octyl, $R_1$ is alkyl containing from 6 to 10 carbon atoms, inclusive; where R is nonyl, $R_1$ is alkyl containing from 3 to 9 carbon atoms, inclusive; where R is decyl, $R_1$ is alkyl containing from 3 to 7 carbon atoms, inclusive; and where R is undecyl, dodecyl, or tridecyl, $R_1$ is alkyl containing from 2 to 7 carbon atoms, inclusive.

The term "alkyl" is intended to include both straight chain and branched chain hydrocarbons — for example, n-heptyl, s-heptyl, isobutyl, t-octyl. This definition extends to both R and $R_1$ and applied wherever the term "alkyl" is used or wherever the prefix denoting the chain configuration for an alkyl of a specified number of carbon atoms is not given—for example, hepty, octyl, nonyl, decyl.

By "miticidally effective amount" is meant the amount of the herein disclosed miticidal compounds which when applied to the habitat of mites in any conventional manner will kill or substantially injure a significant portion of the population thereon.

DETAILED DESCRIPTION OF THE INVENTION

The compounds of the present invention are manufactured by reacting the properly selected isothiocyanate with the properly selected amine. A variety of non-reactive solvents can be used, such as benzene and other aromatic hydrocarbons, ether, dioxane, tetrahydrofuran, and in some instances, alcohols. The time and temperature requirements for the reaction will depend on the reactivities of both the isothiocyanate and the amine used. Normally, a complete reaction will occur with a few hours of reflux. The examples shown herein are illustrative of the method of preparation of the compounds of the invention.

EXAMPLE I 1-n-nonyl-3-n-heptyl-2-thiourea (Compound No. 52 in Table I below)

7.9 g (0.05 mole) n-heptylisothiocyanate was dissolved in 50 ml of benzene. To this solution was added 7.2 g (0.05 mole) of n-nonylamine. The resultant mixture was heated on a steam bath for 1 hour with reflux. The solvent was then removed in a rotary evaporator under vacuum leaving 15.2 g of a waxy solid. The structure, as confirmed by infrared spectroscopy, was that of 1-heptyl-3-nonyl-2-thiourea. The theoretical yield was 15.0 g.

EXAMPLE II 1-n-dodecyl-3-n-butyl-2-thiourea (Compound No. 75 in Table I below)

9.25 g (0.05 mole) of n-dodecylamine was dissolved in 50 ml of benzene. To this solution was added 5.75 g (0.05 mole) of n-butylisothiocyanate. An exothermic reaction took place. When a temperature rise could no longer be detected, the reaction mixture was heated with reflux on a steam bath for 2 hours. The solvent was then removed under vacuum in a rotary evaporator, leaving a residue of 14.5 g of a waxy solid, of melting point 49° to 55° C. The structure, as confirmed by infrared spectroscopy, was that of 1-n-dodecyl-3-n-butyl-2-thiourea. The theoretical yield was 14.2 g.

Other compounds, such as those included in the following table, can be prepared in a manner analogous to that shown in the examples above, starting with the appropriate materials. The compounds in the table are representative of those embodied in the present invention. Compound numbers have been assigned to them for purposes of identification throughout the balance of this specification.

TABLE I $$R-NH-\overset{\overset{S}{\|}}{C}-NH-R_1$$

| Compound No. | R | $R_1$ | $N_D^{30}$ or m.p. ° C |
|---|---|---|---|
| 1 | —CH(C$_6$H$_5$)$_2$ | n-C$_7$H$_{15}$ | 1.5840 |
| 2 | —CH(C$_6$H$_5$)$_2$ | s-C$_7$H$_{15}$ | 1.5751 |
| 3 | —CH(C$_6$H$_5$)$_2$ | n-C$_8$H$_{17}$ | waxy solid |
| 4 | —CH(C$_6$H$_5$)$_2$ | n-C$_9$H$_{19}$ | 87–90° C |
| 5 | —CH(C$_6$H$_5$)$_2$ | n-C$_{10}$H$_{21}$ | 62–70° C |
| 6 | —(CH$_2$)$_3$—O—CH$_2$CH(C$_2$H$_5$)(CH$_2$)$_3$CH$_3$ | n-C$_4$H$_9$ | 1.5003 |
| 7 | —(CH$_2$)$_3$—O—CH$_2$CH(C$_2$H$_5$)(CH$_2$)$_3$CH$_3$ | n-C$_5$H$_{11}$ | 1.4939 |
| 8 | —(CH$_2$)$_3$—O—CH$_2$CH(C$_2$H$_5$)(CH$_2$)$_3$CH$_3$ | n-C$_6$H$_{13}$ | 1.4884 |
| 9 | —(CH$_2$)$_3$—O—CH$_2$CH(C$_2$H$_5$)(CH$_2$)$_3$CH$_3$ | n-C$_7$H$_{15}$ | 1.4956 |
| 10 | —(CH$_2$)$_3$—O—CH$_2$CH(C$_2$H$_5$)(CH$_2$)$_3$CH$_3$ | n-C$_8$H$_{17}$ | 1.4915 |
| 11 | —(CH$_2$)$_3$—O—CH$_2$CH(C$_2$H$_5$)(CH$_2$)$_3$CH$_3$ | n-C$_{12}$H$_{25}$ | 1.4905 |
| 12 | —CH$_2$CH=CH$_2$ | n-C$_9$H$_{19}$ | 1.5180 |
| 13 | —CH$_2$CH=CH$_2$ | n-C$_{10}$H$_{21}$ | 1.5155 |
| 14 | —CH$_2$CH=CH$_2$ | n-C$_{12}$H$_{25}$ | 49–55° C |
| 15 | —CH$_2$CH=CH$_2$ | n-C$_{13}$H$_{27}$ | 52–58° C |

TABLE I-continued $$R-NH-\overset{\overset{S}{\|}}{C}-NH-R_1$$

| Compound No. | R | $R_1$ | $N_D^{30}$ or m.p. ° C |
|---|---|---|---|
| 16 |  | n-$C_{12}H_{25}$ | 1.5127 |
| 17 | 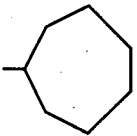 | n-$C_7H_{15}$ | 1.5300 |
| 18 | —CCH$_2$CHCH$_3$ with CH$_3$ CH$_3$ | n-$C_7H_{15}$ | 1.5028 |
| 19 | —CCH$_2$CHCH$_3$ with CH$_3$ CH$_3$ | n-$C_{12}H_{25}$ | 1.4914 |
| 20 | n-$C_7H_{15}$ | n-$C_6H_{13}$ | 1.5065 |
| 21 | n-$C_7H_{15}$ | s-$C_6H_{13}$ | 1.5050 |
| 22 | n-$C_7H_{15}$ | n-$C_7H_{15}$ | waxy solid |
| 23 | n-$C_7H_{15}$ | s-$C_7H_{15}$ | 1.5006 |
| 24 | n-$C_7H_{15}$ | t-$C_8H_{17}$ | 1.4975 |
| 25 | s-$C_7H_{15}$ | n-$C_6H_{13}$ | 1.5025 |
| 26 | s-$C_7H_{15}$ | s-$C_6H_{13}$ | 1.5052 |
| 27 | s-$C_7H_{15}$ | s-$C_7H_{15}$ | 1.4955 |
| 28 | s-$C_7H_{15}$ | t-$C_8H_{17}$ | 1.4970 |
| 29 | n-$C_8H_{17}$ | n-$C_6H_{13}$ | 1.4973 |
| 30 | n-$C_8H_{17}$ | s-$C_6H_{13}$ | 1.4990 |
| 31 | n-$C_8H_{17}$ | n-$C_7H_{15}$ | 1.5015 |
| 32 | n-$C_8H_{17}$ | s-$C_7H_{15}$ | 1.4927 |
| 33 | n-$C_8H_{17}$ | s-$C_8H_{17}$ | 1.4899 |
| 34 | n-$C_8H_{17}$ | t-$C_8H_{17}$ | 1.4995 |
| 35 | n-$C_8H_{17}$ | n-$C_9H_{19}$ | 1.4998 |
| 36 | n-$C_8H_{17}$ | n-$C_{10}H_{21}$ | 1.4903 |
| 37 | s-$C_8H_{17}$ | n-$C_6H_{13}$ | 1.4978 |
| 38 | s-$C_8H_{17}$ | s-$C_6H_{13}$ | 1.5010 |
| 39 | s-$C_8H_{17}$ | n-$C_7H_{15}$ | 1.4993 |
| 40 | s-$C_8H_{17}$ | s-$C_7H_{15}$ | 1.4947 |
| 41 | s-$C_8H_{17}$ | s-$C_8H_{17}$ | 1.4905 |
| 42 | s-$C_8H_{17}$ | t-$C_8H_{17}$ | 1.4934 |
| 43 | t-$C_8H_{17}$ | n-$C_6H_{13}$ | 1.5016 |
| 44 | n-$C_9H_{19}$ | n-$C_3H_7$ | 1.5043 |
| 45 | n-$C_9H_{19}$ | n-$C_4H_9$ | 1.4946 |
| 46 | n-$C_9H_{19}$ | i-$C_4H_9$ | 1.5064 |
| 47 | n-$C_9H_{19}$ | n-$C_5H_{11}$ | 1.4935 |
| 48 | n-$C_9H_{19}$ | i-$C_5H_{11}$ | 1.5035 |
| 49 | n-$C_9H_{19}$ | t-$C_5H_{11}$ | 1.4930 |
| 50 | n-$C_9H_{19}$ | n-$C_6H_{13}$ | 1.4978 |
| 51 | n-$C_9H_{19}$ | s-$C_6H_{13}$ | 1.5032 |
| 52 | n-$C_9H_{19}$ | n-$C_7H_{15}$ | waxy solid |
| 53 | n-$C_9H_{19}$ | s-$C_7H_{15}$ | 1.4962 |
| 54 | n-$C_9H_{19}$ | s-$C_8H_{17}$ | 1.4928 |
| 55 | n-$C_9H_{19}$ | n-$C_9H_{19}$ | waxy solid |
| 56 | n-$C_{10}H_{21}$ | n-$C_3H_7$ | 1.5013 |
| 57 | n-$C_{10}H_{21}$ | i-$C_3H_7$ | 1.4945 |
| 58 | n-$C_{10}H_{21}$ | n-$C_4H_9$ | 1.5043 |
| 59 | n-$C_{10}H_{21}$ | i-$C_4H_9$ | 1.4955 |
| 60 | n-$C_{10}H_{21}$ | n-$C_5H_{11}$ | 1.4962 |
| 61 | n-$C_{10}H_{21}$ | i-$C_5H_{11}$ | 1.4939 |
| 62 | n-$C_{10}H_{21}$ | n-$C_6H_{13}$ | 1.4930 |
| 63 | n-$C_{10}H_{21}$ | s-$C_6H_{13}$ | 1.4986 |
| 64 | n-$C_{10}H_{21}$ | n-$C_7H_{15}$ | waxy solid |
| 65 | n-$C_{10}H_{21}$ | s-$C_7H_{15}$ | 1.4935 |
| 66 | n-$C_{11}H_{23}$ | $C_2H_5$ | 1.5065 |
| 67 | n-$C_{11}H_{23}$ | n-$C_4H_9$ | 1.5007 |
| 68 | n-$C_{11}H_{23}$ | n-$C_5H_{11}$ | 1.4952 |
| 69 | n-$C_{11}H_{23}$ | n-$C_6H_{13}$ | 1.4913 |
| 70 | n-$C_{11}H_{23}$ | n-$C_7H_{15}$ | 1.4973 |
| 71 | n-$C_{11}H_{23}$ | s-$C_7H_{15}$ | 1.4923 |
| 72 | n-$C_{12}H_{25}$ | $C_2H_5$ | 1.4983 |
| 73 | n-$C_{12}H_{25}$ | n-$C_3H_7$ | waxy solid |
| 74 | n-$C_{12}H_{25}$ | i-$C_3H_7$ | 1.4962 |
| 75 | n-$C_{12}H_{25}$ | n-$C_4H_9$ | 56–62° C |
| 76 | n-$C_{12}H_{25}$ | i-$C_4H_9$ | 1.4958 |
| 77 | n-$C_{12}H_{25}$ | s-$C_4H_9$ | 1.4950 |
| 78 | n-$C_{12}H_{25}$ | n-$C_5H_{11}$ | waxy solid |
| 79 | n-$C_{12}H_{25}$ | i-$C_5H_{11}$ | 1.4945 |
| 80 | n-$C_{12}H_{25}$ | n-$C_6H_{13}$ | 1.4914 |
| 81 | n-$C_{12}H_{25}$ | s-$C_6H_{13}$ | 1.4945 |
| 82 | n-$C_{12}H_{25}$ | n-$C_7H_{15}$ | waxy solid |
| 83 | n-$C_{12}H_{25}$ | s-$C_7H_{15}$ | 1.4909 |
| 84 | n-$C_{13}H_{27}$ | $C_2H_5$ | 44–57° C |
| 85 | n-$C_{13}H_{27}$ | n-$C_4H_9$ | 49–64° C |
| 86 | n-$C_{13}H_{27}$ | n-$C_5H_{11}$ | 48–51° C |
| 87 | n-$C_{13}H_{27}$ | n-$C_6H_{13}$ | waxy solid |

Miticidal activity of each of the above compounds was evaluated for efficacy on the two-spotted mite [*Tetranychus urticae* (Koch)] as follows:

I. Plant Dip Assay

Pinto bean plants (*Phaseolus* sp.), approximately 10 cm tall, are transplanted into sandy loam soil in 3-inch clay pots and thoroughly infested with two-spotted mites of mixed ages and sexes. Twenty-four hours later the infested plants are inverted and dipped for 2–3 seconds in 50—50 acetone-water solutions of the test chemicals. Treated plants are held in the greenhouse, and 7 days later mortality is determined for both the adult mites and the nymphs hatching from eggs which were on the plants at the time of treatment. Test concentrations range from about 0.2% down to that at which 50% mortality occurs (LD-50).

II. Systemic Assay

Test chemicals are dissolved in acetone and aliquots are diluted in 200 cc of water in glass bottles. Two pinto bean plants (*Phaseolus* sp.), with expanded primary leaves, are supported in each bottle by cotton plugs, so that their roots and stems are immersed in the treated water. The plants are then infested with 75–100 two-spotted mites of various ages and sexes. One week later the mortality of the adult mites and nymphs is recorded. Test concentrations range from 10 ppm down to that at which 50% mortality occurs (LD-50).

The results of the above test procedures, indicating the effective concentration at which LD-50 control effect was achieved, are listed in Table II.

TABLE II

Effective Concentrations on Two-Spotted Mite [*Tetranychus urticae* (Koch)]

| Compound Number | PE (%) | Eggs (%) | SYS (%) |
|---|---|---|---|
| 1 | .003 | >.05 | >10 |
| 2 | .01 | >.05 | >10 |
| 3 | .005 | .03 | >10 |
| 4 | .01 | >.05 | >10 |
| 5 | .05 | >.05 | >10 |
| 6 | .005 | .005 | >10 |
| 7 | .01 | >.05 | >10 |
| 8 | >.05 | .05 | — |
| 9 | .005 | .005 | >10 |
| 10 | .03 | .05 | >10 |
| 11 | .03 | .05 | >10 |
| 12 | .05 | >.05 | 10 |
| 13 | .05 | .05 | >10 |
| 14 | .01 | .03 | >10 |
| 15 | .008 | .03 | >10 |
| 16 | .005 | .03 | >10 |
| 17 | .01 | >.05 | >10 |
| 18 | .05 | .05 | — |
| 19 | >.05 | .05 | — |
| 20 | .03 | >.05 | >10 |
| 21 | .2 | >.2 | — |
| 22 | >.05 | .05 | — |
| 23 | .03 | .03 | >10 |

TABLE II-continued

Effective Concentrations on Two-Spotted Mite
[*Tetranychus urticae* (Koch)]

| Compound Number | PE (%) | Eggs (%) | SYS (%) |
|---|---|---|---|
| 24 | .05 | .1 | — |
| 25 | .05 | .15 | — |
| 26 | .05 | >.05 | >10 |
| 27 | .07 | .08 | — |
| 28 | .15 | >.2 | — |
| 29 | .008 | >.05 | >10 |
| 30 | .008 | .01 | >10 |
| 31 | .005 | .03 | — |
| 32 | .05 | .05 | — |
| 33 | .05 | >.05 | — |
| 34 | .05 | .07 | — |
| 35 | .005 | .05 | >10 |
| 36 | .05 | .05 | — |
| 37 | .05 | .05 | — |
| 38 | .03 | >.05 | >10 |
| 39 | .01 | >.05 | >10 |
| 40 | .03 | .05 | — |
| 41 | .03 | >.05 | >10 |
| 42 | .05 | .2 | — |
| 43 | .15 | >.2 | — |
| 44 | .05 | >.05 | 10 |
| 45 | .01 | >.05 | >10 |
| 46 | >.05 | .05 | >10 |
| 47 | .005 | .008 | >10 |
| 48 | .03 | >.05 | >10 |
| 49 | .09 | .1 | — |
| 50 | .03 | .03 | >10 |
| 51 | .01 | >.05 | >10 |
| 52 | .001 | >.05 | >10 |
| 53 | .008 | >.05 | >10 |
| 54 | .005 | .03 | >10 |
| 55 | .01 | .01 | >10 |
| 56 | .01 | .03 | >10 |
| 57 | .03 | >.05 | >10 |
| 58 | .005 | .03 | 10 |
| 59 | .008 | >.05 | >10 |
| 60 | .05 | .05 | — |
| 61 | .05 | .03 | >10 |
| 62 | .06 | .06 | — |
| 63 | .01 | >.05 | >10 |
| 64 | .003 | .03 | >10 |
| 65 | .008 | >.05 | >10 |
| 66 | .01 | >.05 | >10 |
| 67 | .005 | >.05 | >10 |
| 68 | .01 | .03 | >10 |
| 69 | .01 | >.05 | >10 |
| 70 | .03 | >.05 | >10 |
| 71 | .008 | >.05 | >10 |
| 72 | .003 | >.05 | >10 |
| 73 | .003 | .03 | >10 |
| 74 | .01 | .05 | — |
| 75 | .003 | .008 | >10 |
| 76 | .003 | >.05 | >10 |
| 77 | .08 | .03 | — |
| 78 | .008 | .03 | >10 |
| 79 | .005 | >.05 | >10 |
| 80 | .005 | .03 | >10 |
| 81 | .005 | .01 | >10 |
| 82 | .008 | >.05 | >10 |
| 83 | .005 | >.05 | >10 |
| 84 | .003 | .03 | >10 |
| 85 | .003 | >.05 | >10 |
| 86 | .005 | .03 | 5 |
| 87 | .01 | >.05 | 10 |

Neither the examples nor the tables above are intended to limit the invention in any manner.

The compounds of this invention are generally embodied in a form suitable for convenient application. For example, the compounds can be embodied in miticidal compositions in the form of emulsions, suspensions, solutions, dusts, and aerosol sprays. In addition to the active compounds, such compositions generally contain the adjuvants which are normally found in miticide preparations. One such composition can contain either a single miticidally active compound or a combination of miticidally active compounds. The miticide compositions of this invention can contain as adjuvants organic solvents such as sesame oil, xylene, or heavy petroleum; water; emulsifying agents; surface active agents; talc; pyrophyllite; diatomite; gypsum; clays; or propellants such as dichlorodifluoromethane; or a combination of these. If desired, however, the active compounds can be applied directly to feedstuffs, seeds, or other such matter upon which the pests feed. When applied in such a manner, it will be advantageous to use a compound which is not volatile. In connection with the activity of the presently disclosed miticidal compounds, it should be fully understood that the compounds need not be active as such. The purposes of this invention will be fully served by a compound which is rendered active by an external influence such as light, or by some physiological action which the compound induces when it is ingested into the body of the pest.

The precise manner in which the miticidal compounds of this invention should be used in any particular instance will be readily apparent to a person skilled in the art. The concentration of the active miticide in a typical composition can vary within rather wide limits. Ordinarily, the miticide will comprise not more than about 15.0% by weight of the composition. The preferred range of concentration of the miticide is about 0.1 to about 1.0% by weight.

What is claimed is:

1. A compound having the formula

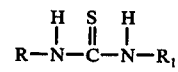

wherein R is benzyhydryl, and $R_1$ is alkyl containing from 7 to 11 carbon atoms, inclusive.

2. A compound according to claim 1 wherein such compound is selected from the group consisting of
   1-benzhydryl-3-n-heptyl-2-thiourea,
   1-benzhydryl-3-s-heptyl-2-thiourea,
   1-benzhydryl-3-n-octyl-2-thiourea,
   1-benzhydryl-3-n-nonyl-2-thiourea, and
   1-benzhydryl-3-n-decyl-2-thiourea.

3. A compound having the formula

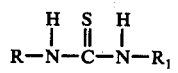

wherein R is 3'-(2'-ethylhexoxy)-propyl, and $R_1$ is alkyl containing from 1 to 12 carbon atoms, inclusive.

4. A compound according to claim 3 wherein such compound is selected from the group consisting of
   1-[3'-(2'-ethylhexoxy)-propyl]-3-n-butyl-2-thiourea,
   1-[3'-(2'-ethylhexoxy)-propyl]-3-n-pentyl-2-thiourea,
   1-[3'-(2'-ethylhexoxy)-propyl]-3-n-hexyl-2-thiourea,
   1-[3'-(2'-ethylhexoxy)-propyl]-3-n-heptyl-2-thiourea,
   1-[3'-(2'-ethylhexoxy)-propyl]-3-n-heptyl-2-thiourea,
   1-]3'-(2'-ethylhexoxy)-propyl]-3-n-octyl-2-thiourea, and
   1-[3'-(2'-ethylhexoxy)-propyl]-3-n-dodecyl-2-thiourea.

5. A method of controlling mites consisting of applying to said mites a miticidally effective amount of a compound having the formula

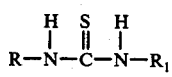

wherein R is selected from the group consisting of benzhydryl, 3'-(2'-ethylhexoxy)-propyl, allyl, cyclohexyl, cycloheptyl, 1',3'-dimethylbutyl, and alkyl containing from 7 to 13 carbon atoms, inclusive; and where R is benzhydryl, $R_1$ is alkyl containing from 7 to 11 carbon atoms, inclusive; where R is 3'-(2-ethylhexoxy)-propyl, $R_1$ is alkyl containing from 1 to 12 carbon atoms, inclusive; where R is allyl, $R_1$ is alkyl containing from 9 to 13 carbon atoms, inclusive; where R is cyclohexyl, $R_1$ is dodecyl; where R is cycloheptyl, $R_1$ is heptyl; where R is 1'-3'-dimethylbutyl, $R_1$ is n-heptyl or dodecyl; where R is heptyl, $R_1$ is alkyl containing from 6 to 8 carbon atoms, inclusive; where R is octyl, $R_1$ is alkyl containing from 6 to 10 carbon atoms, inclusive; where R is nonyl, $R_1$ is alkyl containing from 3 to 9 carbon atoms, inclusive; where R is decyl, $R_1$ is alkyl containing from 3 to 7 carbon atoms, inclusive; and where R is undecyl, dodecyl, or tridecyl, $R_1$ is alkyl containing from 2 to 7 carbon atoms, inclusive.

6. A method according to claim 5 wherein R is benzyhdryl.

7. A method according to claim 6 wherein such compound is selected from the group consisting of
1-benzhydryl-3-n-heptyl-2-thiourea,
1-benzhydryl-3-s-heptyl-2-thiourea,
1-benzhydryl-3-n-octyl-2-thiourea,
1-benzhydryl-3-n-nonyl-2-thiourea, and
1-benzhydryl-3-n-decyl-2-thiourea.

8. A method according to claim 5 wherein R is 3'-(2'-ethylhexoxy)-propyl.

9. A method according to claim 8 wherein such compound is selected from the group consisting of
1-[3'-(2'-ethylhexoxy)-propyl]-3-n-butyl-2-thiourea,
1-[3'-(2'-ethylhexoxy)-propyl]-3-n-pentyl-2-thiourea,
1-[3'-(2'-ethylhexoxy)-propyl]-3-n-hexyl-2-thiourea,
1-[3'-(2'-ethylhexoxy)-propyl]-3-n-heptyl-2-thiourea,
1-[3'-(2'-ethylhexoxy)-propyl]-3-n-octyl-2-thiourea, and
1-[3'-(2'-ethylhexoxy)-propyl]-3-n-dodecyl-2-thiourea.

10. A method according to claim 5 wherein R is allyl.

11. A method according to claim 10 wherein such compound is selected from the group consisting of
1-allyl-3-n-nonyl-2-thiourea,
1-allyl-3-n-decyl-2-thiourea,
1-allyl-3-n-dodecyl-2-thiourea, and
1-allyl-3-n-tridecyl-2-thiourea.

12. A method according to claim 5 wherein R is cyclohexyl.

13. A method according to claim 12 wherein such compound is 1-cyclohexyl-3-n-dodecyl-2-thiourea.

14. A method according to claim 5 wherein R is cycloheptyl.

15. A method according to claim 14 wherein such compound is 1-cycloheptyl-3-n-heptyl-2-thiourea.

16. A method according to claim 5 wherein R is 1',3'-dimethylbutyl.

17. A method according to claim 16 wherein such compound is
1,(1',3'-dimethylbutyl)-3-n-heptyl-2-thiourea, or
1-(1',3'-dimethylbutyl)-3-n-dodecyl-2-thiourea.

18. A method according to claim 5 wherein R is heptyl.

19. A method according to claim 18 wherein such compound is selected from the group consisting of
1-n-heptyl-3-n-hexyl-2-thiourea,
1-n-heptyl-3-s-hexyl-2-thiourea,
1,3-di-n-heptyl-2-thiourea,
1-n-heptyl-3-s-heptyl-2-thiourea,
1-n-heptyl-3-t-octyl-2-thiourea,
1-s-heptyl-3-n-hexyl-2-thiourea,
1-s-heptyl-3-s-hexyl-2-thiourea,
1-s-heptyl-3-s-heptyl-2-thiourea, and
1-s-heptyl-3-t-octyl-2-thiourea.

20. A method according to claim 5 wherein R is octyl.

21. A method according to claim 20 wherein such compound is selected from the group consisting of
1-n-octyl-3-n-hexyl-2-thiourea,
1-n-octyl-3-s-hexyl-2-thiourea,
1-n-octyl-3-n-heptyl-2-thiourea,
1-n-octyl-3-s-heptyl-2-thiourea,
1-n-octyl-3-s-octyl-2-thiourea,
1-n-octyl-3-t-octyl-2-thiourea,
1-n-octyl-3-n-nonyl-2-thiourea,
1-n-octyl-3-n-decyl-2-thiourea,
1-s-octyl-3-n-hexyl-2-thiourea, 1-s-octyl-3-s-hexyl-2-thiourea,
1-s-octyl-3-n-heptyl-2-thiourea,
1-s-octyl-3-s-heptyl-2-thiourea,
1,3-di-s-octyl-2-thiourea,
1-s-octyl-3-t-octyl-2-thiourea, and
1-t-octyl-3-n-hexyl-2-thiourea.

22. A method according to claim 5 wherein R is nonyl.

23. A method according to claim 22 wherein such compound is selected from the group consisting of
1-n-nonyl-3-n-propyl-2-thiourea,
1-n-nonyl-3-n-butyl-2-thiourea,
1-n-nonyl-3-isobutyl-2-thiourea,
1-n-nonyl-3-n-pentyl-2-thiourea,
1-n-nonyl-3-isopentyl-2-thiourea,
1-n-nonyl-3-t-pentyl-2-thiourea,
1-n-nonyl-3-n-hexyl-2-thiourea,
1-n-nonyl-3-s-hexyl-2-thiourea,
1-n-nonyl-3-n-heptyl-2-thiourea,
1-n-nonyl-3-s-heptyl-2-thiourea,
1-n-nonyl-3-s-octyl-2-thiourea, and
1,3-di-n-nonyl-2-thiourea.

24. A method according to claim 5 wherein R is decyl.

25. A method according to claim 24 wherein such compound is selected from the group consisting of
1-n-decyl-3-n-propyl-2-thiourea,
1-n-decyl-3-isopropyl-2-thiourea,
1-n-decyl-3-n-butyl-2-thiourea,
1-n-decyl-3-isobutyl-2-thiourea,
1-n-decyl-3-n-pentyl-2-thiourea,
1-n-decyl-3-isopentyl-2-thiourea,
1-n-decyl-3-n-hexyl-2-thiourea,
1-n-decyl-3-s-hexyl-2-thiourea,
1-n-decyl-3-n-heptyl-2-thiourea, and
1-n-decyl-3-s-heptyl-2-thiourea.

26. A method according to claim 5 wherein R is undecyl.

27. A method according to claim 26 wherein such compound is selected from the group consisting of
1-n-undecyl-3-ethyl-2-thiourea,
1-n-undecyl-3-n-butyl-2-thiourea,
1-n-undecyl-3-n-pentyl-2-thiourea,
1-n-undecyl-3-n-hexyl-2-thiourea,
1-n-undecyl-3-n-heptyl-2-thiourea, and
1-n-undecyl-3-s-heptyl-2-thiourea.

28. A method according to claim 5 wherein R is dodecyl.

29. A method according to claim 28 wherein such compound is selected from the group consisting of
1-n-dodecyl-3-ethyl-2-thiourea,
1-n-dodecyl-3-n-propyl-2-thiourea, 1-n-dodecyl-3-isopropyl-2-thiourea,
1-n-dodecyl-3-isobutyl-2-thiourea,
1-n-dodecyl-3-s-butyl-2-thiourea,
1-n-dodecyl-3-isopentyl-2-thiourea,
1-n-dodecyl-3-n-hexyl-2-thiourea,
1-n-dodecyl-3-s-hexyl-2-thiourea,
1-n-dodecyl-3-n-heptyl-2-thiourea, and
1-n-dodecyl-3-s-heptyl-2-thiourea.

30. A method according to claim 28 wherein such compound is 1-n-dodecyl-3-n-butyl-2-thiourea.

31. A method according to claim 28 wherein such compound is 1-n-dodecyl-3-n-pentyl-2-thiourea.

32. A method according to claim 5 wherein R is tridecyl.

33. A method according to claim 32 wherein such compound is selected from the group consisting of
1-n-tridecyl-3-ethyl-2-thiourea,
1-n-tridecyl-3-n-butyl-2-thiourea,
1-n-tridecyl-3-n-pentyl-2-thiourea, and
1-n-tridecyl-3-n-hexyl-2-thiourea.

34. A miticidally effective composition of matter comprising
(1) a miticidally effective amount of a compound having the formula

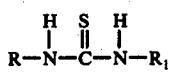

wherein R is benzhydryl and $R_1$ is alkyl containing from 7 to 11 carbon atoms, inclusive; and (2) an inert diluent carrier.

35. A composition according to claim 34 wherein such compound is selected from the group consisting of
1-benzhydryl-3-n-heptyl-2-thiourea,
1-benzhydryl-3-s-heptyl-2-thiourea,
1-benzhydryl-3-n-octyl-2-thiourea,
1-benzhydryl-3-n-nonyl-2-thiourea, and
1-benzhydryl-3-n-decyl-2-thiourea.

36. A miticidally effective composition of matter comprising
(1) a miticidally effective amount of a compound having the formula

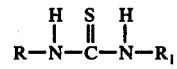

wherein R is 3'-(2'-ethylhexoxy)-propyl and $R_1$ is alkyl containing from 1 to 12 carbon atoms, inclusive; and (2) an inert diluent carrier.

37. A composition according to claim 36 wherein such compound is selected from the group consisting of
1-[3'-(2'-ethylhexoxy)-propyl]-3-n-butyl-2-thiourea,
1-[3'-(2'-ethylhexoxy)-propyl]-3-n-pentyl-2-thiourea,
1-[3'-(2'-ethylhexoxy)-propyl]-3-n-hexyl-2-thiourea,
1-[3'-(2'-ethylhexoxy)-propyl]-3-n-heptyl-2-thiourea,
1-[3'-(2'-ethylhexoxy)-propyl]-3-n-octyl-2-thiourea, and
1-[3'-(2'-ethylhexoxy)-propyl]-3-n-dodecyl-2-thiourea.